United States Patent [19]

Schleppinghoff et al.

[11] Patent Number: 5,008,466
[45] Date of Patent: Apr. 16, 1991

[54] PROCESS FOR THE ISOMERIZATION OF ALKENES HAVING A TERMINAL DOUBLE BOND TO GIVE ALKENES HAVING AN INTERNAL DOUBLE BOND

[75] Inventors: Bernhard Schleppinghoff; Hans-Dieter Köhler; Christian Gabel; Hans-Volker Scheef, all of Dormagen, Fed. Rep. of Germany

[73] Assignee: EC Erdolchemie GmbH, Cologne, Fed. Rep. of Germany

[21] Appl. No.: 336,926

[22] Filed: Apr. 12, 1989

[30] Foreign Application Priority Data

Apr. 16, 1988 [DE] Fed. Rep. of Germany ....... 3812683

[51] Int. Cl.$^5$ ............ C07C 41/00; C07C 43/00; C07C 5/00
[52] U.S. Cl. ................... 568/697; 585/260; 585/515; 585/526; 585/668
[58] Field of Search ............ 585/260, 515, 526, 668; 568/697

[56] References Cited

U.S. PATENT DOCUMENTS

| | | | |
|---|---|---|---|
| 3,326,866 | 6/1967 | Haag | 585/668 |
| 4,232,177 | 11/1980 | Smith | 585/515 |
| 4,284,835 | 8/1981 | Kim et al. | 585/277 |
| 4,482,775 | 11/1984 | Smith | 585/668 |
| 4,672,147 | 6/1987 | Fareasiu | 585/668 |

FOREIGN PATENT DOCUMENTS 455083 12/1974 U.S.S.R. .
WO89/02882 4/1989 World Int. Prop. O. .

*Primary Examiner*—Curtis R. Davis
*Attorney, Agent, or Firm*—Sprung Horn Kramer & Woods

[57] ABSTRACT

Alkenes having a terminal double bond can be isomerized to give alkenes having an internal double bond if alkenes having a terminal double bond or hydrocarbon feedstock having a content of alkenes of this type having a terminal double bond are subjected to treatment, in the presence of hydrogen, over a macroporous or gel-like cation exchanger in the H+ form which contains 0.001 to 10 g of one or more metals of the VIth and/or VIIth and/or VIIIth sub-group of the periodic system of the elements in elementary form per liter of dry cation exchanger and which has a degree of cross-linking of 2 to 65% and a specific surface area of 5 to 750 m$^2$/g of dry exchange resin. The treatment is carried out in the liquid phase at a temperature from 0° to 120° C.

20 Claims, No Drawings

PROCESS FOR THE ISOMERIZATION OF ALKENES HAVING A TERMINAL DOUBLE BOND TO GIVE ALKENES HAVING AN INTERNAL DOUBLE BOND

BACKGROUND OF THE INVENTION

The invention relates to a process for the isomerization of alkenes having a terminal double bond to give alkenes having an internal double bond in the presence of hydrogen on a cation exchanger in the H+ form which is coated with a hydrogenation-active metal.

Linear alkenes, including those in which a possible branching does not originate at a C atom forming the double bond, have in the past proved valuable raw materials for various reactions. Thus, alkenes having a terminal double bon are valued as monomers or comonomers for the preparation of polyolefins having valuable properties on the other hand, alkenes having an internal double bond are in demand as alkylating agents for the alkylation of n-alkanes and/or isoalkanes, which gives valuable motor fuels ("alkylate petrol"). In these alkylation reactions, alkenes having an internal double bond are preferred to those having a terminal double bond, because their alkylates have better properties in the fuel field. Thus, for example, n-but-1-ene with n-butane/isobutane gives an alkylate petrol having a Reseach Octane Number RON of 91, whereas n-but-2-ene under the same conditions gives an alkylate having an RON of 97.

The hydrocarbon mixtures formed in cracking plants (for example steam crackers of FCC=fluid catalyst crackers) are, above all, a suitable source of alkenes of the type mentioned. The alkenes having a terminal or internal double bond of the same number of C atoms which are present in such mixtures from crackers are in a thermodynamic equilibrium which depends on the properties of the particular pair of alkenes. At high cracker temperatures, this thermodynamic equilibrium is more strongly in the side of the alkene having the terminal double bond, whereas at lower temperatures it is shifted more and more towards the alkenes having an internal double bond.

There has, therefore, been no lack of attempt to isomerize catalytically alkenes having a terminal double bond into alkenes having an internal double bond and to bring the ratio of the one to the other nearer to the thermodynamic equilibrium at a temperature lower than the cracker temperature. An isomerization of this type is possible, for example, on a palladium catalyst, varying statements having been made in the literature concerning necessary auxiliaries. Thus it is reported in FR No. 7,828,723 that a little carbon monoxide must be added for isomerization in the presence of hydrogen. Furthermore, the supports for palladium catalysts of this type are high-purity, and therefore inert, mineral substances. In DE-OS (German Published Specification) No. 3,140,573, for example, high-purity $Al_2O_3$ containing 0.3% by weight of Pd is mentioned, the heat of neutralization of the catalyst, measured as the heat of neutralization when ammonia is absorbed, having the extremely low value of 6 cal/g.

The DE-OS (German Published Specification) mentioned describes, in addition, a two-stage upgrading process for a $C_4$-olefin fraction, in which process the isobutene present in the olefin fraction is oligomerized in a first stage on a fluorinated aluminium oxide, boron-/aluminium oxide or silicon dioxide/aluminium oxide, and in which, in the second stage, n-but-1-ene is partly isomerized to give n-but-2-ene in the presence of hydrogen in a separate catalyst bed on the Pd catalyst described above.

BRIEF DESCRIPTION OF THE INVENTION

It has now been found, surprisingly, that a catalyst suitable for the isomerization mentioned can also be a non-inert cation exchange resin in the H+ form, although the danger of undesired reactions, such as resinification and undesired alkylation reactions, would have been expected on account of the numerous strongly acid groups present. In addition, a support of this type offers further advantages, described later in the text, for the isomerization catalyst.

The invention relates, accordingly, to a process for the isomerization of alkenes having a terminal double bond to give alkenes having an internal double bond by treating alkenes having a terminal double bond or hydrocarbon feedstocks containing alkenes of this type having a terminal double bond over catalyst containing hydrogenation-active metals in the presence of hydrogen, which is characterized in that the treatment is carried out in the liquid phase at a temperature from 0° to 120° C. on a macroporous or gel-like acid cation exchanger in the H+ form which contains 0.001 to 10 g of one or more metals of the VIth and/or VIIth and/or VIIIth sub-group of the periodic system of the elements in elementary form per litre of dry cation exchanger and which has a degree of crosslinking of 2 to 65% and a specific surface area of 5 to 750 $m^2/g$ of dry exchange resin.

DETAILED DESCRIPTION OF THE INVENTION

Macroporous or gel like acid cation exchangers to be employed in accordance with the invention are known to those skilled in the art and can be prepared, for example, by copolymerization of vinyl monomers and divinyl crosslinking agents, if appropriate in the presence of solvents (DE-AS (German Published Specification) No. 1,113,570; and U.S. Pat. No. 3,586,646), or by the condensation of phenol and formaldehyde. Examples of vinyl monomers are styrene or acrylic acid esters; an example of a divinyl crosslinking agent is divinylbenzene. Examples of acid groups in cation exchangers of this type are carboxyl groups, phosphonic acid groups or sulphonic acid groups. It is preferable to employ styrene/divinyl-benzene polymers containing strongly acid sulphonic acid groups; these are commercially available under various names.

The degree of crosslinking (amount of divinyl crosslinking agent, relative to the total amount of comonomers) is 2 to 65%, preferably 8 to 25%. The specific surface area of the cation exchanger is 5 to 750 $m^2/g$, preferably 50 to 250 $m^2/g$. The average pore radius varies within the limits of 50 to 1,200 Å, preferably 70 to 500 Å. Cation exchangers of this type, for example in the form of bead polymers, have particle sizes of 0.1 to 2 mm and, as a powder resin, have particle sizes of 10 to 100 μm.

The cation exchangers are employed in the H+ form, after they have been coated with 0.001 to 10 g, preferably 0.2 to 3 g, relative to 1 l of dry cation exchanger, of one or more metals of the VIth and/or VIIth and/or VIIIth sub-group of the periodic system of the elements (Mendeleev) in elementary form. The following are examples of such metals: chromium, molybdenum, tungsten, manganese, rhenium, iron, cobalt, nickel, ruthenium, rhodium, palladium, osmium, iridium and platinum. The following may be mentioned as preferred: palladium, platinum, rhenium, molybdenum or nickel; palladium, platinum and nickel are very particularly preferred. One or more of the metals mentioned, but preferably only one of the metals mentioned, can be present on the cation exchanger.

The cation exchanger can, for example, be coated with one or more of the metals mentioned by bringing a non-complex, cationic salt of these metals into contact in a manner which is in itself known with the cation exchanger in the $H^+$ form. If appropriate, the acid liberated in the course of this is neutralized by means of suitable compounds having an alkaline reaction, for example solutions of alkali metal hydroxides. The amount of metal salt to be applied is calculated or determined by simple preliminary tests, so that the amount of metal subsequently desired in elementary form is applied to the cation exchanger.

The metal-doped cation exchanger is washed until neutral, dried, for example at 80° to 100° C. in vacuo, and then treated with hydrogen, for example at 2 to 50 bar, preferably 20 to 30 bar, and a temperature of 50° to 140° C., preferably 80° to 120° C., in order to convert the metals applied into the elementary state. In principle, it is also possible to make use of other reducing agents, such as hydrazine or formaldehyde.

The process according to the invention is carried out in the liquid phase at a temperature from 0° to 120° C., preferably 20° to 90° C. The pressure in the process is adjusted to a level at which the reaction mixture is at least partially liquid, with the exception of any undissolved $H_2$. The correlation between the working temperature selected and setting up a pressure of this kind is familiar to those skilled in the art. The metal-doped cation exchanger is present, in the reaction, in a fixed bed or in a fluid bed. It is subjected to an hourly loading, expressed by means of the LHSV (liquid hourly space velocity), of 0.1 to 10, preferably 0.5 to 8 and particularly preferably 1 to 5, liters of hydrocarbon feedstock per liter of catalyst.

Alkenes having 4 to 7 C atoms, preferably 4 to 5 C atoms and particularly preferably 4 C atoms, and a terminal double bond are employed in the process according to the invention. Alkenes of this type are but-1-ene, pent-1-ene, hex-1-ene and hept-1-ene.

Alkenes of this type having terminal double bonds can be prepared in refineries and petrochemical plants from petroleum distillation cuts or preferably from distillation cuts from steam crackers or catalytic crackers. Hydrocarbon feedstocks containing alkenes of this type having terminal double bonds are also of technical importance, there being present, in addition, linear and branched alkanes within the C atom range mentioned from 4 to 7 or the corresponding alkenes having internal double bonds or both classes of compounds mentioned together. Whereas, in principle, mixtures within the range of 4 to 7 C atoms mentioned can be treated in accordance with the invention, just as in the case of the above-mentioned pure alkenes having a terminal double bond, it is, however, preferable and corresponds with industrial practice, to employ broader or narrower distillation cuts within the range of 4 to 7 C atoms mentioned. Examples of broader or narrower distillation cuts of this type are a $C_5$–$C_7$ cut, a $C_6$–$C_7$ cut, a $C_5$–$C_6$ cut and a $C_4$–$C_5$ cut, but particularly preferably a $C_4$ distillation cut. The so-called $C_4$ raffinate II is typical of a $C_4$ cut. This originates from the crude $C_4$ distillation cut of the reaction products from a steam cracker or catalytic cracker. The crude $C_4$ cut is generally first subjected to an extraction in order to remove the valuable product butadiene, in the course of which the so-called $C_4$ raffinate I is formed. The $C_4$ raffinate I is subjected to catalytic oligomerization or catalytic etherification of isobutene in order to remove this isobutene, the $C_4$ raffinate II then being the residue. In the $C_4$ raffinate II the contents of the compounds mentioned vary within the following limits: n-butane 15 to 30% by volume, isobutane 2 to 8% by volume, but-1-ene 15 to 50% by volume, but-2-ene 20 to 40% by volume and isobutene 0.1 to 3% by volume.

Hydrogen can be employed in the process according to the invention in a pure or technical state. For example, a hydrogen obtained in petrochemical plants and associated with methane and/or nitrogen or an $H_2$-containing residual gas from petrochemical plants can be employed advantageously from the economic point of view. The $H_2$ content in technical or pure hydrogen of this type is 70 to 100% of $H_2$ by volume, while in residual gases it is often about 80 to 90% of $H_2$ by volume.

In the isomerization according to the invention the hydrogen is not consumed, but acts as a catalyst. In principle, therefore, its proportion is optional, for example from 5 to 300 mole %, relative to the content of alkene having a terminal double bond. In the upper section of the range mentioned, however, it will already be necessary to expect a noticeable hydrogenation of the alkene having a terminal double bond, which is particularly susceptible to hydrogenation reactions, whereas the alkene having an internal double bond is somewhat more stable to a hydrogenation of this kind. In the lower section of the range mentioned it will be necessary to expect lower reaction rates, particularly if it is intended to carry out the reaction within the range of fairly low temperatures and within the range of fairly high LHSV values. The reaction will, therefore, preferably be carried out in the presence of less than stoichiometric proportions of hydrogen, relative to the amount of the alkene having a terminal double bond, for example in the range from 5 to 95, particularly preferably 10 to 50, mole % of $H_2$, relative to the alkene having a terminal double bond.

A high proportion of hydrogen, even up to the range of proportions greater than stoichiometric, can be advantageous if, within the range of high LHSV values, much hydrogen flows through the isomerization reactor unused.

In the process according to the invention, the alkene having a terminal double bond is converted into the alkene having an internal double bond to the extent of 80 to 90%, often up to about 95%, of the value permitted by the thermodynamic equilibrium.

Mention has already been made of the hydrogenation activity of the metal-doped cation exchanger to be employed in accordance with the invention on the more reactive alkene having a terminal double bond within the range of high proportions of hydrogen. This hydrogenation activity on the alkene having a terminal double bond falls off very greatly within the range of lower proportions of $H_2$, in particular proportions less than stoichiometric, so that it is possible to carry out in the manner described the isomerization according to the invention of the alkenes without substantial losses of alkenes through hydrogenation. It has been noticed, however, that the metal-doped cation exchanger to be employed in accordance with the invention has a hydrogenation activity even in the range of low proportions of hydrogen, but that this activity is limited to highly unsaturated accompanying compounds and, in the case of the latter, effects a selective hydrogenation down to the monoalkene. Highly unsaturated accompanying compounds which may be mentioned here are alkadienes having isolated, conjugated or cumulative double bonds, alkines and alkenines. Individual compounds within the range of $C_4$ distillation cuts are 1,3-butadiene, 1,2-butadiene, but-1-ine, but-2-ine and vinylacetylene. Further highly unsaturated accompanying compounds in a $C_4$ distillation cut can be propine or allene, that is to say traces of incompletely separable constituents of $C_3$ hydrocarbons, as, in general, all distillation cuts contain small traces of hydrocarbons having adjacent numbers of C atoms. The process according to the invention for the isomerization of alkenes can, therefore, be combined in a preferred form with a selective hydrogenation of highly unsaturated accompanying compounds.

The invention also relates, therefore, to a process for carrying out at the same time
- (a) the isomerization of alkenes having a terminal double bond to give alkenes having an internal double bond in the manner described above and
- (b) the selective hydrogenation of highly unsaturated accompanying compounds in hydrocarbon feedstocks, which is characterized in that, in the process described above, it is possible to permit, and to use, feedstocks containing highly unsaturated accompanying compounds of this type, and then to employ additional hydrogen in a proportion of 100 to 200% of the proportion required by stoichiometry for the selective hydrogenation of the highly unsaturated accompanying compounds.

This proportion of hydrogen which is required for selective hydrogenation is generally already present in the proportion of hydrogen required for the isomerization in the case of low contents of highly unsaturated accompanying compounds, relative to the alkenes to be isomerized. The total proportion of hydrogen can then be limited within the range from 10 to 80 mole %, preferably 15 to 50 mole %, relative to the molar amount of alkene having a terminal double bond which is to be isomerized.

As well as the isomerization activity and the hydrogenation activity of the metal-doped cation exchanger according to the invention, the latter also possesses, however, acid groups in the H+ form which can be used advantageously for simultaneously carrying out a reaction catalysed by acid groups of this type. An example of a reaction of this type, catalysed by acid groups, is the oligomerization of isoalkenes.

The invention also relates, therefore, to a process for carrying out at the same time
- (a) the isomerization of alkenes having a terminal double bond to give alkenes having an internal double bond in the manner described above and
- (b) the catalysed oligomerization of isoalkenes in hydrocarbon feedstocks, which is characterized in that, in the process described above, feedstocks containing isoalkenes of this type are used.

This oligomerization of isoalkenes which takes place at the same time is of particular technical importance in the field of the $C_4$ hydrocarbons; in this case the hydrocarbon feedstock thus consists of a mixture of n-butane (5 to 10% from either a steam cracker or from a catalytic cracker), isobutane (2 to 5% or about 25 to 40%, respectively), isobutene (40 to 50% or 12 to 22%, respectively), but-1-ene (20 to 30% or 10 to 15%, respectively) and but-2-ene (10 to 25% or about 20 to 30%, respectively), as well as up to 3% of more highly unsaturated hydrocarbons. The products of simultaneously carrying out the isomerization and the oligomerization then consist of the oligomerizate (diisobutylene, triisobutylene, tetraisobutylene and small amounts of higher oligomers) and a $C_4$ raffinate II which can be separated therefrom and in which the content of but-1-ene originally present has been converted into but-2-ene to the extent of 90 to 95%.

A further conversion of isoalkenes which is catalysed by acid groups in the H+ form is, as is known, their etherification with alkanols with the formation of the corresponding ethers, such as methyl tert.-butyl ether (MTBE), tert.-amyl methyl ether (TAME) and the corresponding ethers formed from higher isoalkenes or with the incorporation of alkanols other than methanol, for example ethanol, propanol, isopropanol, butanol or isobutanol.

The invention also relates, therefore, to a process for carrying out at the same time
- (a) the isomerization of alkenes having a terminal double bond to give alkenes having an internal double bond in the manner described above and
- (b) the catalysed etherification of isoalkenes in feedstocks of this type, which is characterized in that in the process described above, feedstocks containing isoalkenes of this type are permitted, and used, and, in addition, alkanols having 1 to 4 C atoms are employed in a proportion of 0.7 to 4 moles, preferably 0.8 to 2.5 moles and particularly preferably 1 to 2 moles, per mole of the isoalkenes.

The process according to the invention for the isomerization of alkenes can be combined in a particularly preferred manner with the selective hydrogenation of highly unsaturated accompanying compounds and with the catalysed reaction of isoalkenes, particularly the catalysed etherification of isoalkenes.

The invention also relates, therefore, in a particularly preferred manner to a process for carrying out at the same time
- (a) the isomerization of alkenes having a terminal double bond to give alkenes having an internal double bond in the manner described above,
- (b) the selective hydrogenation of highly unsaturated accompanying compounds in hydrocarbon feedstocks and
- (c) the catalysed etherification of isoalkenes in feedstocks of this type, which is characterized in that, in the process described above, feedstocks containing highly unsaturated accompanying compounds of this type and containing isoalkenes of this type are used, and, in addition, hydrogen is employed in a proportion of 100 to 200% of the proportion required by stoichiometry for the selective hydrogenation of the highly unsaturated accompanying compounds, and alkanols having 1 to 4 C atoms are employed in an amount of 0.7 to 4 moles, preferably 0.8 to 2.5 moles and particularly preferably 1 to 2 moles, per mole of the isoalkenes.

Process conditions within the ranges described above for the temperature, the LHSV and the other conditions mentioned are used in all the advantageous processes mentioned, including oligomerization.

The inventive idea, on which the process according to the invention is based, of using the metal-doped cation exchanger described above for the isomerization of alkenes having a terminal double bond to give alkenes having an internal double bond relates, therefore, in the last-mentioned variant, to the simultaneous utilization of the multi-functional activity of this metal-doped cation exchanger, namely the isomerization activity, the selective hydrogenation activity and the activity for the catalysed reaction of isoalkenes.

The invention therefore also embraces the use of a macroporous or gel-like cation exchanger in the $H^+$ form which contains 0.001 to 10 g of one or more metals of the VIth and/or VIIth and/or VIIIth sub-group of the periodic system of the elements in elementary form per liter of dry cation exchanger and which has a degree of crosslinking of 2 to 65% and a specific surface area of 5 to 750 m²/g of dry exchange resin, for carrying out at the same time (a) the isomerization of alkenes having a terminal double bond to give alkenes having an internal double bond in hydrocarbon feedstocks in the presence of hydrogen, (b) the selective hydrogenation of highly unsaturated accompanying compounds in feedstocks of this type in the presence of hydrogenation hydrogen and (c) the catalysed etherification of isoalkenes in feedstocks of this type with $C_1$-$C_4$-alkanols.

EXAMPLE 1

Preparation of a Cation Exchanger to be Employed in Accordance with the Invention Sufficient palladium acetate was made available to the commercially available cation exchanger LEWATIT SPC 118 (a styrene/divinylbenzene copolymer having sulphonic acid groups and made by Bayer AG, prepared by a process corresponding to DE-AS (German Published Specification) No. 1,113,570) in the water-moist $H^+$ form for 1 g of Pd per liter of dry resin to be present on the cation exchanger after reduction with $H_2$. The acetic acid liberated in the course of the treatment with palladium acetate was neutralized with 1% strength by weight NaOH. The cation exchanger was washed until neutral and dried for 24 hours at 100° C. in a waterpump vacuum. The palladium present on the cation exchanger was reduced to the metal at 90° to 100° C. and a hydrogen pressure of 20 to 25 bar in the course of 48 hours.

EXAMPLE 2

Oligomerization of Raffinate I Over a Pd-Doped Cation Exchanger as Described in Example 1 in the Presence of Hydrogen C4-Raffinate I was converted into the corresponding oligomers and a C4-raffinate II rich in but-2-ene in a flow apparatus equipped with two jacket-heated steel reactors of identical construction, arranged in tandem.

The apparatus was operated continuously; after it had been operated consistently for 48 hours, analytical samples were taken every hour and were evaluated by gas chromatography.

The reaction was carried out as follows:

| | |
|---|---|
| C4-Raffinate feed | liquid |
| Direction of product flow | upwards |
| Hydrogen | parallel to the product |
| Reactor 1: Pd cation exchanger (as described in Example 1) | with recycling (fresh feed/recycling = 1:1) |
| Reactor 2: cation exchanger (as described in Example 1, but no Pd) | continuous flow |
| Stripper | liquid/gas phase |
| Separator for C4 exit gas | condensation of the gas phase |
| Raffinate | |

The following reaction conditions were established:

| | |
|---|---|
| Reaction pressure | 15.0 bar |
| Reactor 1 LHSV/temperature | 4.6/20° C. |
| Reactor 2 LHSV/temperature | 2.3/75° C. |
| Hydrogen | 2.0 l/hr. |
| Molar ratio of hydrogen to butadiene | 5.0 |

The results obtained are listed in Table 1.

TABLE 1

| | | Total product | | |
|---|---|---|---|---|
| Product Sampling point | Raffinate I Feed | after reactor 1 $H+$/Pd | after reactor 2 $H+$ | Raffinate II Exit gas |
| Component | | | | |
| Total (g/h) | 500.0 | 500.0 | 500.0 | 258.7 |
| Butanes (g/h) | 73.0 | 74.5 | 74.5 | 74.5 |
| Isobutene (g/h) | 220.5 | 218.5 | 2.5 | 2.5 |
| But-1-ene (g/h) | 116.0 | 41.5 | 21.8 | 21.8 |
| But-2-ene (g/h) | 89.5 | 163.5 | 157.2 | 157.2 |
| Total butenes (g/h) | 426.0 | 423.5 | 181.5 | 181.5 |
| Butadiene (g/h) | 1.0 | <0.01 | <0.01 | <0.01 |
| Total C8 (g/h) | <0.1 | 2.0 | 149.5 | 2.7 |
| Total C12 (g/h) | <0.1 | <0.1 | 81.5 | <0.1 |
| Total C16 (g/h) | <0.1 | <0.1 | 12.0 | <0.1 |
| Total C20 (g/h) | <0.1 | <0.1 | 1.0 | <0.1 |
| Total olig.(g/h) | <0.1 | 2.0 | 244.0 | 2.7 |
| Butadiene hydrogenation (%) | | >99.0 | | |
| Hydrogenation of n-Butenes (%) | | 0.7 | | |
| Ratio of Butene-2 to Butene-1 | 0.77 | 3.9 | 7.2 | 7.2 |
| iso-C4 oligomerization(%) | | 0.9 | 98.9 | |
| n-C4 oligomerization(%) | | <0.1 | 12.7 | |

EXAMPLE 3

The test was carried out analogously to Example 2, the recycling/fresh feed ratio in reactor 1 being reduced to 0.5:1.

In addition, the reaction temperature in reactor 1 was raised.

The following reaction conditions were established:

| | |
|---|---|
| Reaction pressure | 15 bar |
| Reactor 1 LHSV/temperature | 3.5/65° C. |
| Reactor 2 | 2.3/75° C. |
| Hydrogen | 2.0 l/hr. |
| Molar ratio of hydrogen to butadiene | 5.0 |

TABLE 2

| Product Sampling point | Raffinate I Feed | Total product after reactor 1 H+/Pd | Total product after reactor 2 H+ | Raffinate II Exit gas |
|---|---|---|---|---|
| Component | | | | |
| Total (g/h) | 500.0 | 500.0 | 500.0 | 254.1 |
| Butanes (g/h) | 65.0 | 67.0 | 67.0 | 67.0 |
| Isobutene (g/h) | 226.0 | 90.3 | 3.0 | 3.0 |
| But-1-ene (g/h) | 116.5 | 29.0 | 22.6 | 22.6 |
| But-2-ene (g/h) | 91.5 | 163.2 | 159.0 | 159.0 |
| Total butenes (g/h) | 434.0 | 282.5 | 184.6 | 184.6 |
| Butadiene (g/h) | 1.0 | <0.01 | <0.01 | <0.01 |
| Total C8 (g/h) | <0.1 | 132.0 | 151.0 | 2.5 |
| Total C12 (g/h) | <0.1 | 17.0 | 81.0 | <0.1 |
| Total C16 (g/h) | <0.1 | 1.0 | 14.9 | <0.1 |
| Total C20 (g/h) | <0.1 | 0.5 | 1.5 | <0.1 |
| Total oligomers (g/h) | <0.1 | 150.5 | 248.4 | 2.5 |
| Butadiene hydrogenation (%) | | >99.0 | | |
| Hydrogenation of n-Butene (%) | | 0.7 | | |
| Ratio of Butene-2 to Butene-1 | 0.8 | 5.6 | 7.0 | |
| iso-C$_4$ oligomerization(%) | | | 60.0 | 98.7 |
| n-C$_4$ oligomerization(%) | | | 7.6 | 12.5 |

EXAMPLE 4

Comparison Example

The test was carried out analogously to Example 3. Cation exchanger without Pd was employed as the catalyst in both reactors.

Metering in of hydrogen was omitted.

TABLE 3

| Product Sampling point | Raffinate I Feed | Total after reactor 2 H+ | Raffinate II Exit gas |
|---|---|---|---|
| Component | | | |
| Total (g/h) | 500.0 | 500.0 | 264.9 |
| Butanes (g/h) | 73.0 | 73.0 | 73.0 |
| Isobutene (g/h) | 204.0 | 2.4 | 2.4 |
| But-1-ene (g/h) | 122.5 | 40.2 | 40.2 |
| But-2-ene (g/h) | 99.0 | 146.1 | 146.1 |
| Total butenes (g/h) | 425.5 | 188.7 | 188.7 |
| Butadiene (g/h) | 1.5 | 0.2 | 0.2 |
| Total C8 (g/h) | <0.1 | 145.8 | 3.0 |
| Total C12 (g/h) | <0.1 | 83.3 | <0.1 |
| Total C16 (g/h) | <0.1 | 8.5 | <0.1 |
| Total C20 (g/h) | <0.1 | 0.5 | <0.1 |
| Total oligomers (g/h) | <0.1 | 238.1 | 3.0 |
| Butadiene dimerization (%) | | 86.7 | |
| Ratio of Butene-2 to Butene-1 | 0.8 | 3.6 | |
| iso-C$_4$ Oligomerization(%) | | 98.8 | |
| n-C$_4$ Oligomerization(%) | | 15.9 | |

EXAMPLE 5

The test was carried out analogously to Example 2, but the isobutene was etherified with methanol to give MTBE, instead of the oligomerization.

The following reaction conditions were set up:

| | |
|---|---|
| Reaction pressure | 10.0 bar |
| Reactor 1 LHSV/temperature | 2.0/65° C. |
| Reactor 2 LHSV/temperature | 1.0/65° C. |
| Hydrogen | 3.0 l/hr. |
| Molar ratio of hydrogen to butadiene | 5.0 |

TABLE 4

| Product Sampling point | Raffinate I Feed | Total after reactor 2 Pd/H+ | Raffinate II Exit gas |
|---|---|---|---|
| Component | | | |
| Total (g/h) | 630.0 | 630.0 | 309.8 |
| Butanes (g/h) | 73.0 | 75.0 | 75.0 |
| Isobutene (g/h) | 204.0 | 3.0 | 3.0 |
| But-1-ene (g/h) | 122.5 | 24.5 | 24.5 |
| But-2-ene (g/h) | 99.0 | 199.5 | 196.5 |
| Total butenes (g/h) | 425.5 | 224.0 | 224.0 |
| Butadiene (g/h) | 1.5 | <0.01 | <0.01 |
| Methanol (g/h) | 130.0 | 15.2 | 10.8 |
| MTBE (g/h) | <0.1 | 315.8 | <0.1 |
| Butadiene hydrogenation (%) | | >99.0 | |
| Hydrogenation of Butenes (%) | | 0.2 | |
| Ratio of Butene-2 to Butene-1 | 0.8 | 8.0 | |
| iso-C$_4$ Etherification (%) | | 98.5 | |

EXAMPLE 6

Comparison Example

The etherification was carried out analogously to Example 3, the isobutene being etherified with methanol to give MTBE.

The reaction was carried out without the addition of hydrogen.

The following reaction conditions were established:

| | |
|---|---|
| Reaction pressure | 10. bar |
| Reactor 1 LHSV/temperature | 2.0/65° C. |
| Reactor 2 LHSV/temperature | 1.0/65° C. |

TABLE 5

| Product Sampling point | Raffinate I Feed | Total after reactor 2 H+ | Raffinate II Exit gas |
|---|---|---|---|
| Component | | | |
| Total (g/h) | 630.0 | 630.0 | 312.2 |
| Butanes (g/h) | 73.0 | 73.0 | 72.8 |
| Isobutene (g/h) | 204.0 | 5.1 | 5.1 |
| But-1-ene (g/h) | 122.5 | 120.0 | 119.7 |
| But-2-ene (g/h) | 99.0 | 101.5 | 101.2 |
| Total butenes (g/h) | 425.5 | 226.6 | 226.0 |
| Butadiene (g/h) | 1.5 | 1.4 | 1.4 |
| Methanol (g/h) | 130.0 | 16.5 | 12.0 |
| MTBE (g/h) | <0.1 | 312.1 | <0.1 |
| Higher homologues | | 0.4 | |
| Ratio Butene-2 to Butene-1 | 0.8 | 0.8 | |
| iso-C$_4$ Etherification (%) | | 97.5 | |

EXAMPLE 7

The test was carried out analogously to Example 2.

Reactor 2 was bypassed; butadiene was hydrogenated and the but-1-ene was isomerized to give but-2-ene. The following reaction conditions were established:

| Reaction pressure | 15.0 bar |
|---|---|
| Reactor 1 LHSV/temperature | 6.0/40° C. |
| Hydrogen | 2.0 l/hr. |
| Molar ratio of hydrogen to butadiene | 5.0 |

TABLE 6

| Product Sampling point | Raffinate I Feed | Total after reactor Pd/H+ |
|---|---|---|
| Component | | |
| Total (g/h) | 500.0 | 500.0 |
| Butanes (g/h) | 73.0 | 75.5 |
| Isobutene (g/h) | 204.0 | 204.0 |
| But-1-ene (g/h) | 122.5 | 28.0 |
| But-2-ene (g/h) | 99.0 | 192.5 |
| Total butenes (g/h) | 425.5 | 424.5 |
| Butadiene (g/h) | 1.5 | 0.01 |
| Butadiene hydrogenation (%) | | >99.0 |
| Hydrogenation n-C4: to C4 (%) | | 0.5 |
| Ratio Butene-2 to Butene-1 | 0.8 | 6.9 |

EXAMPLE 8

The test was carried out analogously to Example 7. A C5 cut was selected as the feed. The following reaction conditions were established:

| Reaction pressure | 15.0 bar |
|---|---|
| Reactor 1 LHSV/temperature | 3.0/40° C. |
| Hydrogen | 9.0 l/hr. |
| Molar ratio of hydrogen to dienes | 3.0 |

TABLE 7

| Product Sampling point | C5 cut Feed | Total after reactor Pd/H+ |
|---|---|---|
| Component | | |
| Total (g/h) | 500.0 | 500.0 |
| Pentanes (g/h) | 166.0 | 169.5 |
| 3-MB-1 (g/h) | 1.0 | 0.1 |
| 2-MB-1 (g/h) | 13.5 | 5.1 |
| 2-MB-2 (g/h) | 56.0 | 65.3 |
| Total methyl-butenes | 70.5 | 70.5 |
| C5-Dienes(g/h) | 3.5 | 0.01 |
| Residual hydrocarbons | 260.0 | 260.0 |
| C5-Diene hydrogenation(%) | | >99.0 |
| Ratio of 2MB-2 to 2MB-1 | 4.1 | 13.0 |

3MB-1 (3-methylbut-1-ene)
2MB-1 (2-methylbut-1-ene)
2MB-2 (2-methylbut-2-ene)

EXAMPLE 9

Comparison Example

The test was carried out like Example 8. The catalyst employed was the cation exchanger according to Example 1 without Pd and without the addition of hydrogen.

The following reaction conditions were established:

| Reaction pressure | 15.0 bar |
|---|---|
| Reactor 1 LHSV/temperature | 3.0/40° C. |

TABLE 8

| Product Sampling point | C5 cut Feed | Total after reactor H+ |
|---|---|---|
| Component | | |
| Total (g/h) | 500.0 | 500.0 |
| Pentanes (g/h) | 166.0 | 166.0 |
| 3-MB-1 (g/h) | 1.0 | 1.0 |
| 2-MB-1 (g/h) | 13.5 | 13.0 |
| 2-MB-2 (g/h) | 56.0 | 56.5 |
| Total methyl-butenes | 70.5 | 70.5 |
| C5 dienes (g/h) | 3.5 | 1.0 |
| Higher homologues | <0.1 | 2.5 |
| Residual hydrocarbons | 260.0 | 260.0 |
| Oligomerization of C5 dienes(%) | | 71.4 |
| Ratio of 2MB-2 to 2MB-1 | 4.1 | 4.3 |

3-MB-1 (3-methylbut-1-ene)
2-MB-1 (2-methylbut-1-ene)
2-MB-2 (1-methylbut-1-ene)

What is claimed is:

1. A process for the isomerization of alkenes having a terminal double bond to give alkenes having an internal double bond by treating alkenes having a terminal double bond or hydrocarbon feedstocks containing alkenes having a terminal double bond over catalysts containing hydrogenation-active metals in the presence of hydrogen, characterized in that the treatment is carried out in the liquid phase at a temperature from 0° to 120° C. on a macroporous or gel acid cation exchanger in the H+ form which contains 0.001 to 10 g of one or more metals of the VIth and/or VIIth and/or VIIIth sub-group of the periodic system of the elements (Medeleev) in elementary form per liter of dry cation exchanger and which has a degree of crosslinking of 2 to 65% and a specific surface area of 5 to 750 m$^2$/g of dry exchange resin.

2. The process of claim 1, characterized in that the cation exchanger is a styrene/divinyl-benzene polymer containing sulphonic acid groups.

3. The process of claim 1, characterized in that the degree of crosslinking is of from 8 to 25%.

4. The process of claim 1, characterized in that the specific surface area of the cation exchanger is 50–250 m$^2$/g.

5. The process of claim 1, characterized in that the pore radius of the cation exchanger varies within the limits of 50–1,200 Å.

6. The process of claim 5, characterized in that the pore radius varies in the limits of 70–500 Å.

7. The process of claim 1, characterized in that the cation exchanger contains 0.2–3 g, relative to 1 liter of dry cation exchanger, of one or more metals of the VIth and/or VIIth and/or VIIIth sub-group of the periodic system of the elements (Mendeleev) in elementary form.

8. The process of claim 1, characterized in that the metals are palladium, platinum, rhenium, molybdenum or nickel.

9. The process of claim 8, characterized in the metals are palladium, platinum or nickel.

10. The process according to claim 1, characterized in that the treatment is carried out at 20° to 90° C.

11. The process according to claim 1, characterized in that an LHSV (liquid hourly space velocity) of 0.1 to 10 liters of feed material per liter of catalyst and per hour is established for the treatment.

12. The process of claim 1, characterized in that alkenes having 4–7 C atoms are employed.

13. The process of claim 12, characterized in that alkenes having 4–5 C atoms are employed.

14. The process according to claim 1, characterized in that, in addition to the alkenes having a terminal double bond, the feed material contains alkenes having an internal double bond and/or alkanes.

15. The process for carrying out at the same time
  (a) the isomerization of alkenes having a terminal double bond to give alkenes having an internal double bond in accordance with claim 1, and
  (b) the selective hydrogenation of highly unsaturated accompanying compounds in hydrocarbon feed materials,
characterized in that, in the process according to claim 1, feed materials containing highly unsaturated accompanying compounds of this type are used and additional hydrogen is employed in a proportion of 100 to 200% of the proportion required by stoichiometry for the selective hydrogenation of the highly unsaturated accompanying compounds.

16. The process for carrying out at the same time
  (a) the isomerization of alkenes having an terminal double bond to give alkenes having an internal double bond in accordance with claim 1, and
  (b) the catalysed oligomerization of isoalkenes in hydrocarbon feed materials,
characterized in that, in the process according to claim 1, feed materials containing said isoalkenes are used.

17. The process for carrying out at the same time
  (a) the isomerization of alkenes having a terminal double bond to give alkenes having an internal double bond in accordance with claim 1, and
  (b) the catalysed etherification of isoalkenes in feed materials,
characterized in that, in the process according to claim 1, feed materials containing said isoalkenes are used and, in addition, alkanols having 1 to 4 C atoms are employed in a proportion of 0.7 to 4 moles per mole of the isoalkenes.

18. The process for carrying out at the same time
  (a) the isomerization of alkenes having a terminal double bond to give alkenes having an internal double bond in accordance with claim 1,
  (b) the selective hydrogenation of highly unsaturated accompanying compounds in hydrocarbon feed materials, and
  (c) the catalysed etherification of isoalkanes in said feed materials,
characterized in that, in the process according to claim 1, said feed materials containing highly unsaturated accompanying compounds and containing said isoalkenes are used and, in addition, hydrogen is employed in a proportion of 100 to 200% of the proportion required by stoichiometry for the selective hydrogenation of the highly unsaturated accompanying compounds, and alkanols having 1 to 4 C atoms are employed in a proportion of 0.7 to 4 moles per mole of the isoalkenes.

19. The process of claim 18, characterized in that the alkanols are employed in a proportion of 0.8 to 2.5 moles per mole of the isoalkenes.

20. The process of claim 19, characterized in that the alkanols are employed in a proportion of 1 to 2 moles per mole of the isoalkenes.

* * * * *